United States Patent [19]

Suzuki et al.

[11] Patent Number: 4,548,622
[45] Date of Patent: Oct. 22, 1985

[54] DEVICE FOR SEPARATING DISSOLVED GASES AND ENTRAINED BUBBLES FROM LIQUID

[75] Inventors: Ryushi Suzuki; Joji Yamaga, both of Tokyo, Japan

[73] Assignee: Ishikawajima-Harima Jukogyo Kabushiki Kaisha, Japan

[21] Appl. No.: 597,258

[22] Filed: Apr. 6, 1984

[30] Foreign Application Priority Data

Apr. 12, 1983 [JP] Japan ................ 58-54354[U]

[51] Int. Cl.$^4$ ............................................. B01D 19/00
[52] U.S. Cl. .......................................... 55/204; 55/55
[58] Field of Search ............... 55/55, 159, 182, 189, 55/191, 194, 204

[56] References Cited

U.S. PATENT DOCUMENTS

| 2,200,620 | 5/1940 | Findley | 55/191 X |
| 2,231,501 | 2/1941 | Jepertinger | 55/191 X |
| 3,616,599 | 11/1971 | Burnham | 55/55 X |
| 3,670,850 | 6/1972 | Swearinger | 55/182 X |
| 4,322,226 | 3/1982 | Hudec | 55/189 X |

Primary Examiner—Charles Hart

[57] ABSTRACT

A tank for storing a liquid is provided with a circulation passage for circulating the liquid by a suction pump. A pressure at the suction port of the suction pump is maintained at a negative pressure lower than a pressure at which gases dissolved in the liquid and the liquid is circulated, whereby the gases having been dissolved in the liquid are separated and the bubbles entrained by the liquid grow in size. These gases and bubbles are collected, agglomerated and discharged in the line connected to the discharge port of the suction pump.

1 Claim, 4 Drawing Figures

DEVICE FOR SEPARATING DISSOLVED GASES AND ENTRAINED BUBBLES FROM LIQUID

BACKGROUND OF THE INVENTION

The present invention relates to a device for effectively separating gases dissolved and bubbles entrained in a liquid such as working oil, lubricant, boiler water or the like which is simple in construction, compact in size and inexpensive to manufacture.

When gases dissolved in a liquid form bubbles or when a liquid entrains bubbles, these bubbles must be separated from the liquid because they cause damage to equipment, increase compressivity, cause errosion due to cavitation, vibration and noise, result in poor product quality, and cause deterioration and change in quality of liquid.

One of the conventional methods for separating gases from a liquid is such that a liquid is stored in a tank and the gases above the level of liquid is sucked by a vacuum pump so that the pressure within the tank becomes less than a gas separation pressure (that is, a pressure at which gases dissolved in the liquid become bubbles), whereby dissolved gases are separated and floated up. Such method as described above is of a batch type so that the gas-free liquid must be refilled into another tank or the top of the tank must be opened. As a result, the operation is troublesome. In the case of air, when a liquid free from air is exposed to the surrounding atmosphere, air dissolves into the liquid again so that the dissolved air must be separated by the above-described cumbersome method.

Therefore there has been proposed a system in which a liquid is filled in an air-tightly sealed tank so that dissolved air is separated by a vacuum procedure while the liquid is suctioned by a pump. However, the tank must be provided with a vacuum pump and if the head of a liquid-discharge pump is low, the suction side becomes negative in pressure, resulting in failure to discharge the liquid. That is, a gas separation pressure of gases dissolved in a liquid held at rest is lower than a gas separation pressure of gases dissolved in a liquid in motion. As a result, in order to effect the vacuum separation of gases dissolved in a liquid contained in an air-tightly sealed tank, a negative pressure must be considerably increased. As a consequence, the head of a suction pump is decreased so that the pump cannot discharge the liquid. Therefore the pump must be placed at the upper portion of the tank so that there may be provided a sufficient head. As described above, according to the conventional air-tightly sealed tank system, the difficult problem of pressure must be investigated and solved.

DETAILED DESCRIPTION OF THE PREFERRED EMBODIMENT

Figure 1:
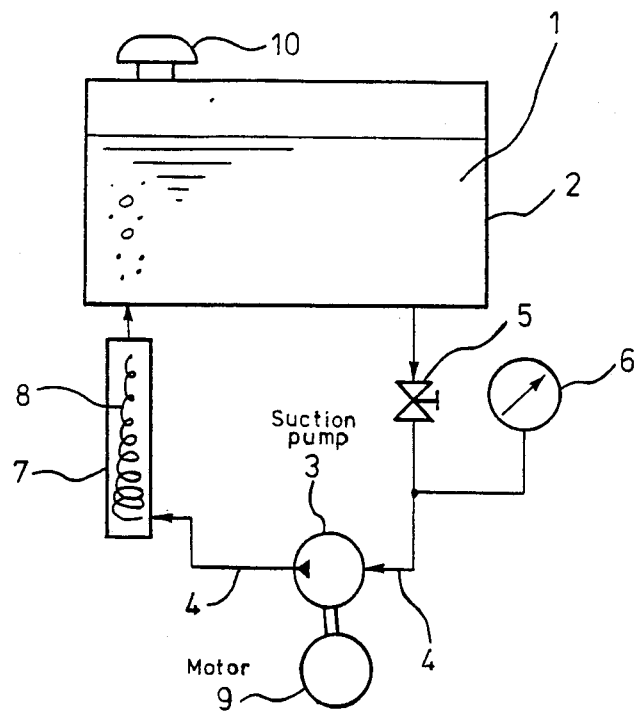
FIG. 1 is a view used to explain a preferred embodiment of the present invention.

FIG. 1 shows a preferred embodiment of the present invention. A tank 2, which stores a liquid 1, is provided with a liquid circulation passage 4 with a suction pump 3 so that the liquid 1 in the tank 2 is sucked by the suction pump 3 and then returned to the tank 2. A throttle valve 5 is inserted between the tank 2 and the suction port of the suction pump 3. A vacuum gage 6 is inserted between the throttle valve 5 and the suction pump 3. A bubble collector 7 is inserted in the circulation passage 4 between the tank 2 and the discharge port of the suction pump 3. In the bubble collector 7, bubbles are collected and grown by a spiral flow 8. The suction pump 3 is driven by a motor 9. The tank 2 is provided with a breather 10. The tank 2 may be of an open type as shown or of a gas-tightly sealed type.

Figure 3:
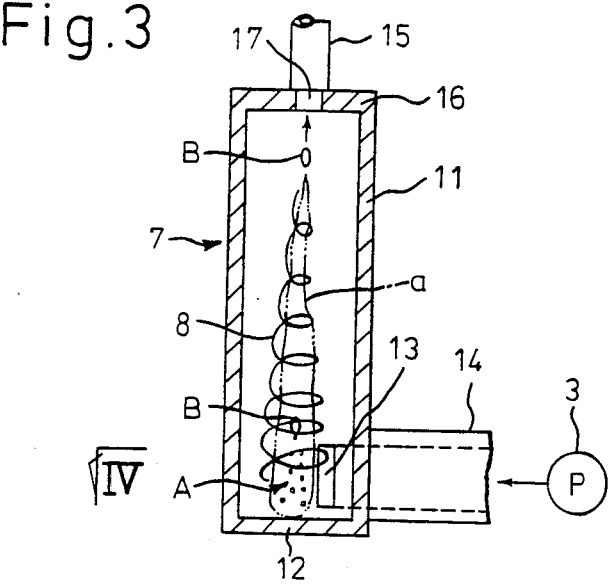
FIG. 3 is a longitudinal sectional view of a bubble collector.
Figure 4:
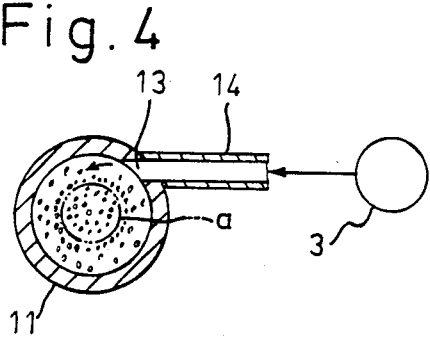
FIG. 4 is a view looking in the direction of the arrow IV of FIG. 3.

FIGS. 3 and 4 show one example of the bubble collector. The bubble collector 7 comprises a hollow cylindrical body 11 which defines a cylindrical space therein. An inlet pipe 14 is connected to an inlet port 13 which is opened adjacent to the bottom 12 of the cylindrical body 11 such that the liquid is caused to flow in the tangential direction. An outlet pipe 15 is connected to an outlet port 17 which is formed through a top 16 of the cylindrical body 11. When a liquid flows through the inlet port 13 into the cylindrical body 11, a spiral flow 8 is produced within the cylindrical body 11 so that the centrifugal force is exerted to the liquid. As a consequence, the pressure along the axis of the spiral flow 8 becomes lower than the pressure at the inner wall surface of the cylindrical body 11. Furthermore the pressure along the axis of the spiral flow 8 is lowest at a in the vicinity of the inlet port and is gradually increased downstream. After the pressure reaches a maximum value, it is gradually decreased. As a result, bubbles entrained in the liquid are forced to move toward the center a of the spiral flow adjacent to the inlet port because of the difference between the pressure at the center A adjacent to the inlet port 13 and the maximum pressure at the downstream of the spiral flow. Therefore bubbles are collected and grown into bubbles B of large size or diameter. Bubbles B flow downstream because the balance between the force causing the bubbles B to the inlet port 13 and the liquid force is lost.

Next the mode of operation will be described.

The throttle valve 5 is so controlled that the negative pressure is produced at the inlet or suction port of the suction pump 3. In this case, the degree of opening of the throttle valve 5 is controlled in response to the reading of the vacuum gage 6. The degree of vacuum is preferably less than the gas separation pressure and is dependent upon the liquid, the gases, the additives, the solubility of gases, the temperature of the liquid, the viscosity of the liquid, the flow rate of the liquid at the suction port of the suction pump, the Reynolds's number, vibration imparted to the liquid and so on. When the pressure is so reduced that the discharge from the suction pump 3 rapidly drops, the bubble forming effect is increased. For instance, in the case of a hydraulically actuated oil piston pump, the pressure is on the order of −500 mm Hg. When the continuous operation of the suction pump 3 is carried out in the manner described above, the pressure between the throttle valve 5 and the suction pump 3 is decreased so that the solubility of gases is decreased and consequently the dissolved gases are supersaturated. As a result, bubbles are easily formed. Bubbles entrained in the liquid flowing in this section grow in size due to the reduction in pressure.

The bubbles formed or enlarged at the suction port of the suction pump 3 are entrained by the liquid which flows into the bubble collector 7. In the bubble collector 7, bubbles in the liquid are collected along the axis of the spiral flow and grow in size and are charged into the tank 2. Enlarged bubbles B have a high buoyancy so that they float at high velocities in the tank and then are discharged without being sucked by the suction pump 3. It is to be understood that instead of the throttle valve 5, an orifice may be used so that the flow rate remains unchanged.

The discharge pressure of the suction pump 3 may be considered to be the sum of the head of the liquid, a small pressure loss in the bubble collector 7 and the resistance encountered in the pipe or circulation passage 4. It is a very small value so that errosion due to cavitation; that is, due to the collapse of bubbles can be prevented at the discharge port. Moreover, sliding members of the suction pump 3 are lubricated by the liquid so that wear or damage of metallic sliding members can be avoided.

When gases dissolved in the liquid are separated so that the non-saturation degree of gases is increased, the velocity or rate at which the gases are dissolved into the liquid is increased and the ability of the liquid for dissolving gases is increased. As a result, even when bubbles are formed or entrained in the section except the section between the throttle valve 5 and the suction pump 3, they vanish within a very short time period or they are reduced in size. Therefore, the rate of bubbles included in the liquid is decreased.

When the bubble collector 7 as shown in FIGS. 3 and 4 is used, a gas column a which is indicated by the broken lines and which is dependent on the flow rate, velocity and viscosity of the liquid flowing through the inlet port 13 into the cylindrical body 11 is formed and part of gases grow into large-sized bubbles which flow downstream. Therefore when the output pipe 15 is connected to the tank, the large-sized bubbles float up by their own buoyancy and are discharged.

Figure 2:
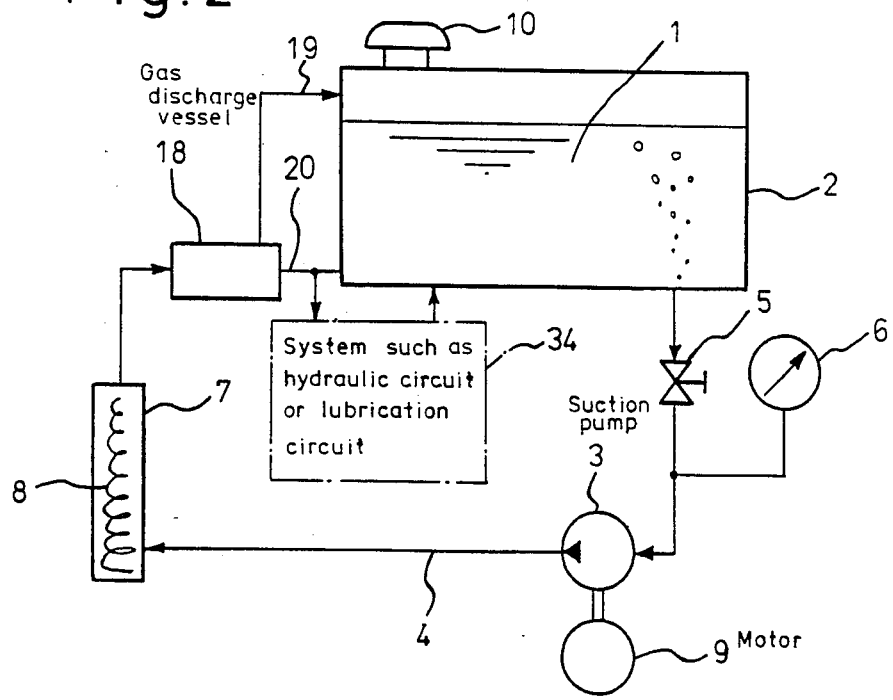
FIG. 2 shows a modification of the embodiment.

It is to be understood that the present invention is not limited to the preferred embodiment described above. For instance, as shown in FIG. 2, the bubble collector 7 is not connected to the tank 2, but is communicated with a gas discharge vessel 18 which may be, for instance, in the form of a large diameter pipe. The collected bubbles float up in the vessel 18 and are discharged through a line 19 to the surrounding atmosphere or the upper space in the tank 2. The liquid free from gases flows through a line 20 into the tank 20. Alternatively, the liquid free from gases is charged into a system 34 including a pump such as a hydraulic circuit or a lubrication circuit and then returned to the tank 2. As described above, according to the present invention, it is of course possible to dispose various equipment and systems after the bubble collector 7. Moreover various modifications may be effected without departing the true spirit of the present invention.

The effects and features of a device for separating gases from a liquid according to the present invention may be summarized as follows:

(I) Gases in a liquid or bubbles entrained in a liquid can be separated in an efficient manner.

(II) The device is very simple in construction and inexpensive to fabricate.

(III) A liquid in a tank can be sucked by a pump and continuously supplied to a system.

(IV) In contrast with the conventional devices, cumbersome suction pressure control can be eliminated.

(V) When one kind of liquid is mixed with another kind of liquid (for instance, water), the latter can be vaporized by the negative pressure between a tank and a suction pump so that it can be floated and separated with other bubbles.

(VI) The operation of the device can be accomplished by suitablly setting a negative pressure between a throttle and a suction pump. There is no need of taking into consideration the relative position between a liquid tank and a suction pump.

What is claimed is:

1. A device for separating dissolved gases and entrained bubbles from a liquid comprising a circulation passage connected to a liquid tank and including a suction pump, the liquid being withdrawn from said tank and circulated by said suction pump, throttle means in the circulation passage fluidically interposed between a suction port of said suction pump and said tank for producing a negative pressure on liquid withdrawn from said tank and decreasing the solubility of gases in the liquid flowing out of said tank and into the suction port of said suction pump to produce a negative pressure lower than a pressure at which gases are dissolved in the liquid, and supersaturating those gasses dissolved in that liquid whereby bubbles can be easily formed, and a bubble collector means in the circulation passage located fluidically downstream of a discharge port of said suction pump and fluidically upstream of said tank for receiving the liquid containing the supersaturated gases from said suction pump and collecting and growing bubbles whereby said bubble collector means cooperates with said throttle means for efficiently separating gases and bubbles from a liquid which has been withdrawn from said tank, said bubble collector means including a cylindrical housing having an inlet located at the bottom of said housing and an outlet located at the top of said housing for causing the liquid to flow tangentially and upwardly with pressure increasing from a first valve adjacent to said inlet to a maximum and then decreasing to a second value.

* * * * *